United States Patent [19]
Duvick et al.

[11] Patent Number: 6,083,736
[45] Date of Patent: Jul. 4, 2000

[54] *OCHROBACTRUM ANTHROPI* BACTERIA WHICH DEGRADE MONILIFORMIN

[75] Inventors: Jon Duvick; Tracy A. Rood, both of Des Moines, Iowa

[73] Assignee: Pioneer Hi-Bred International, Inc., Des Moines, Iowa

[21] Appl. No.: 09/270,693

[22] Filed: Mar. 17, 1999

Related U.S. Application Data

[63] Continuation-in-part of application No. 08/753,317, Nov. 22, 1996, abandoned.

[51] Int. Cl.$^7$ ................ C12N 1/20; C12N 1/00
[52] U.S. Cl. .............. 435/252.1; 435/822; 435/824
[58] Field of Search .............. 435/252.1, 262.5, 435/822, 824

[56] References Cited

U.S. PATENT DOCUMENTS

| | | | |
|---|---|---|---|
| 3,364,192 | 1/1968 | Brillaud | 435/146 |
| 3,997,568 | 12/1976 | Peters et al. | 549/720 |
| 4,004,978 | 1/1977 | McMullen et al. | 435/135 |
| 4,006,265 | 2/1977 | Tamas et al. | 426/623 |
| 4,998,586 | 3/1991 | Toyoda et al. | 424/93.2 |
| 5,248,608 | 9/1993 | Van Dooren et al. | 435/280 |
| 5,297,625 | 3/1994 | Premuzic et al. | 166/246 |

FOREIGN PATENT DOCUMENTS

| | | |
|---|---|---|
| 387693B | 8/1988 | Austria . |
| 450721B1 | 10/1991 | European Pat. Off. . |
| 4205196A1 | 9/1992 | Germany . |
| 96/20595 | 7/1996 | WIPO . |

OTHER PUBLICATIONS

ATCC Catalog at http://www.atcc.org accessed Jan. 09, 1998.
DSM Catalog at http://www.gbf–brauschweig.de/DSMZ accessed Jan. 09, 1998.
BCCM Catalog at http://belspo.be accessed Jan. 09, 1998.
He, et al. 1992. "Microbial transformation of deoxynivalenol." *Appl. Environ. Microbiol.* 58: 3857–3863.
Ueno, Y. 1985. "The toxicology of mycotoxins." CRC Critical Reviews Toxicology 14: 99–132.
Kollarczik, et al. 1994. "In vitro transformation of the Fusarium mycotoxins deoxynivalenol and zearalenone by the normal gut microflora of pigs." Natural Toxins, 2: 105–110.
Westlake, et al. 1989. In vitro metabolism of mycotoxins by bacterial, protozoal and ovine ruminal fluid preparations. Animal Feed Sci. Tech. 25: 169–178.
"Mycofix Plus." Published by BIOMIN Ing. Erber KG., Europlatz 5, A–3100, SA, Pölten, Austria.
Plattner and Nelson. "Production of Beauvericin by a Strain of *Fusarium proliferatum* Isolated from Corn Fodder for Swine." 60: 3894–3896.
Arai et al. 1967. "Antimicrobial activity of aflatoxins." Journal of Bacteriol. 93(1) pp. 59–64 in Chem Abst. 66: 53152.
Logrieco, et al. "Occurrence and toxigenicity of *Fusarium proliferatum* from preharvest maize ear rot, and associated mycotoxins, in Italy." 1995, *Plant Disease*, 79(7), pp. 727–731.
Logrieco, et al. 1993. "Natural Occurrence of beauvericiin in preharvest *Fusarium subglutinans* infected corn ears in Poland." J. Agric. Food Chem, 41, pp. 2149–2152.
Logrieco, et al. 1993. "Occurrence and toxicity of *Fusarium subglutinans* from Peruvian maize." Myopathologia 122: 185–190.
Zhang, et al. 1994. "Detoxification of moniliformin." Weishengwu Zuebao, 34(2), pp. 119–123, Abst. only.

*Primary Examiner*—Jon P. Weber

[57] ABSTRACT

The present invention provides a bacterial microorganism, *Ochrobactrum anthropi*, having the ability to degrade or detoxify moniliformin or structurally related mycotoxins. The present invention further provides a method for detoxification of grain pre- or post-harvest using *Ochrobactrum anthropi* having the ability to degrade or detoxify moniliformin or derivatives or analogs of moniliformin.

2 Claims, No Drawings

OCHROBACTRUM ANTHROPI BACTERIA WHICH DEGRADE MONILIFORMIN

CROSS-REFERENCE TO RELATED APPLICATION

This application is a continuation-in-part of co-pending application U.S. Ser. No. 08/753,317, filed Nov. 22, 1996.

TECHNICAL FIELD

The present invention relates generally to the detection and isolation of moniliformin-degrading organisms and to compositions and methods for detoxification or degradation of moniliformin in grain. This method has broad application in crop agriculture and in the improvement of food grain quality and feed safety.

BACKGROUND OF THE INVENTION

Fungal diseases are common problems in crop agriculture. Many strides have been made against plant diseases as exemplified by the use of hybrid plants, pesticides and unproved agricultural practices. However, as any grower or home gardener can attest, the problems of fungal plant disease continue to cause difficulties in plant cultivation. Thus, there is a continuing need for new methods and materials for solving the problems caused by fungal diseases of plants. These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity.

Within the Fusarium sp. are several important pathogens of corn and other cereals in various countries. In corn, Fusarium is known to cause root, stem and ear rot that results in severe crop reduction. The etiology of Fusarium ear mold is poorly understood, although physical damage to the ear and certain environmental conditions can contribute to its occurrence (Nelson, P. E., 1992, "Taxonomy and Biology of *Fusarium moniliforme.*" Mycopathologia 117: 29–36). Fusarium may be isolated from most field grown maize, when no visible mold is present The relationship between seedling infection and the stalk and ear diseases caused by Fusarium is not clear. Genetic resistance to visible kernel mold has been identified (Gendloff E., Rossman E., Casale W., Isleib T., Hart P., 1986, "Components of resistance to Fusarium ear rot in field corn." Phytopathology 76: 684–688; Holley R. N., Hamilton P. B., Goodman M. M., 1989, "Evaluation of tropical maize germplasm for resistance to kernel colonization by *Fusarium moniliforme.*" Plant Dis 73: 578–580). The mycotoxins produced by the Fusarium species that infect plants may accumulate in infected plants or in stored grains, presenting serious health consequences for livestock, humans and other consumers of meat or other food products of such livestock. Fusarium infection has been associated with chronic or acute mycotoxicoses in both farm animals and man (Botallico, et al.). An important mycotoxin that has been found to be produced by certain Fusarium sp. and has been identified in Fusarium-infected crops is moniliformin.

Moniliformin is a water-soluble toxin produced by Fusarium species such as *Fusarium moniliforme* and *F. moniliforme* var. subglutinans, as well as other species. These Fusarium species are found in virtually all food-grade corn worldwide, and moniliformin-producing isolates have been reported in Europe, South Africa, The United States, New Zealand, Taiwan and South America. It is likely that as more surveys are completed, moniliformin will be found at high levels in certain grain samples from a variety of areas. Moniliformin has been shown to have marked toxic effects toward animals and plants. It selectively inhibits mitochondrial pyruvate and alpha-ketoglutarate oxidations. Grain containing high levels of moniliformin may be restricted in its use or subject to important import/export regulations.

The discovery of bacteria that are able to metabolize moniliformin allows contaminated grain to be detoxified. This invention provides a bacterium that can grow on moniliformin as a sole or major carbon source. The degradation of moniliformin in the media may be assayed by a thin layer chromatography (TLC) assay. The present invention provides a method to reduce the amount of the mycotoxin in corn by incubation of infected corn with this bacterium or, alternatively, with the moniliformin-metabolization enzyme.

There is a need in the art for novel methods with which moniliformin may be eliminated from a plant or harvested grain. It is considered important by those skilled in the art to continue to develop inventions in order to protect the final consumer of a plant or harvested grain. The present invention provides the reagents and methodologies necessary to ameliorate plants and harvested grains from moniliformin.

SUMMARY OF THE INVENTION

In one embodiment, the present invention provides a wild-type organism having the ability to degrade or detoxify moniliformin. The present invention may further include a mutant of the wild-type organism that has the ability to degrade or detoxify moniliformin. The present invention further provides a method for detoxification of infected grain pre- or post-harvest using a microorganism having the ability to degrade or detoxify moniliformin or a derivative or analog of moniliformin.

DISCLOSURE OF THE INVENTION

The present invention is based on the discovery of an organism having the ability to degrade the mycotoxin moniliformin. The present invention has resulted from a search for a biological means of detoxifying moniliformin and comprises a bacterial species, isolated from field-grown maize kernels, capable of growing on moniliformin as a sole or major carbon source, degrading it partially or completely in the process.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g. J. H. Langenheim and K. V. Thimann, Botany: Plant Biology and Its Relation to Human Affairs (1982) John Wiley; Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed., Prentice-Hall; O. D. Dhringra and J. B. Sinclair, Basic Plant Pathology Methods, (1985) CRC Press; Maniatis, Fritsch & Sambrook, Molecular Cloning: A Laboratory Manual (1982); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); the series in Methods in Enzymology (S. Colowick and N. Kaplan, eds., Academic Press, Inc.); and Current Protocols in Molecular Biology (John Wiley & Sons, Inc. 1996).

In describing the present invention, the following terms will be employed, and are intended to be defined as indicated below.

A microbe is defined as any microorganism (including both eukaryotic and prokaryotic organisms) such as fungi, yeasts, bacteria, actinomycetes, algae and protozoa, as well as other unicellular structures capable of growth in culture.

A moniliformin-producing microbe is any microbe capable of producing the mycotoxin moniliformin or analogs thereof. Such microbes are generally members of the fungal genus Fusarium, as well as recombinantly derived organisms which have been genetically altered to enable them to produce moniliformin or analogues thereof.

By degrading moniliformin or having the ability to degrade moniliformin is meant any modification or ability to make any modification to the moniliformin molecule that causes a decrease in or loss of its toxic activity. Such a change can comprise cleavage of any of the various bonds, oxidation, reduction, the addition or deletion of a chemical moiety, or any other change that affects the activity of the molecule. Furthermore, chemically altered moniliformin may be isolated from cultures of microbes that produce an enzyme of this invention, such as by growing the organisms on media containing radioactively-labeled moniliformin, tracing the label, and isolating the degraded toxin for further study. The degraded moniliformin may be compared to the active compound for its toxicity in known sensitive species, such as brine shrimp (*Artenia salina L.*) (Logrieco, 1993).

By structurally related mycotoxin is meant any mycotoxin having a chemical structure related to a moniliformin or analog of moniliformin, as well as other mycotoxins having similar chemical structures that would be expected to be detoxified by activity of the moniliformin degradative enzymes.

By sole or major carbon source is meant that microorganism capable of growing on media containing a carbon source, which is at least 90% moniliformin.

Harvested grain is defined as any form of grain, which has been somehow removed from the environment in which it was grown. For example, harvested grain may comprise ear corn, or corn kernels, for example. Harvested grain may further comprise that in storage or that being processed. Processed grain is grain that has been through some form of processing and will be used in the production of food for human consumption or will be used as animal feed ("feed grain").

Within this application, plant refers to a photosynthetic organism including but not limited to an algae, moss, fern, gymnosperm, or angiosperm. Preferably, said plant is one from which feed grain (preferably for human or animal consumption) may be harvested ("harvested grain"). Most preferably, said plant includes any variety of corn (maize), wheat, sorghum, rice and barley.

A mature plant is defined as a plant in which normal development of all vegetative and reproductive organs has occurred.

A plant cell includes any cell derived from a plant, including callus as well as protoplasts, and embryonic and gametic cells.

The present invention comprises a methodology for the isolation of a microorganism having the ability to degrade moniliformin and a methodology for degradation of moniliformin on a plant in the field as well as on harvested grain. Said microorganism may include but is not limited to bacteria and fungi. In order to isolate said microorganism having the ability to degrade moniliformin, an assay was developed in which said microorganism is initially isolated from a source material. Said source material may comprise any plant or plant-associated material including but not limited to any green tissue such as the stalk, leaf, ear, or kernel. Plant-associated material may include but is not limited to soil in close approximation to the plant. Said microorganism is then cultured in a media having moniliformin as the sole or major carbon source. The media is then monitored for the degradation of moniliformin by thin layer chromatography (TLC).

To test the ability of said microorganism isolated by the above-described methodology to degrade or detoxify moniliformin on plants, mature plants are inoculated with a moniliformin-producing organism and then treated with an appropriate amount of an organism having the ability to degrade moniliformin. The treatment may comprise application of a composition comprising an efficacious amount of an organism having the ability to degrade moniliformin to said plant whereby the moniliformin present is degraded. Preferably, said application consists of topically applying said composition upon the tissues of said plant, such that moniliformin upon said tissues is degraded. Alternatively, said plant or harvested grain may be treated with the said organism following harvest. Mature plants may be inoculated with a moniliformin-producing organism and harvested at an appropriate time.

Following harvest, said plant or harvested grain may be treated with an efficacious amount of said organism having the ability to degrade moniliformin. An important utility for the present invention is the detoxification of moniliformin present in grain following harvest A suitable feed material or "sample" is spiked with a known amount of mycotoxin delivered in a suitable solvent, preferably ethanol, at an appropriate rate, preferably one ml solvent per gram, followed by sufficient mixing to distribute said mycotoxin throughout said material. A control sample receives solvent only. The final concentration of said mycotoxin is preferably between 0.1 and 1.0 mg per gram of feed material. The sample may then be air-dried to remove excess solvent The sample is next innoculated with $10^5$–$10^7$ colony forming units (cfu)/g of log-phase cells of a microorganism having the ability to degrade said mycotoxin, at a sufficient rate, preferably one ml cells per gram, followed by sufficient mixing to distribute said cells throughout said sample. A control sample may comprise cells that have been killed by heating, preferably to approximately 80° C. A control sample may further comprise cells of a microorganism that is not able to degrade said mycotoxin. Said sample is then placed into a container, said container is closed and incubated for a sufficient period of time at an appropriate temperature. Said period of time is preferably within the range of one day to two weeks and said temperature is preferably room temperature or approximately 28° C. Following incubation, the contents of said container are extracted in a suitable organic solvent (or organic aqueous mixture) for recovering said mycotoxin. The resulting extract is then concentrated and subjected to qualitative and quantitative analysis for the presence of said mycotoxin. The amount of said mycotoxin detected in said extract is then compared to the amount of said mycotoxin detected in said control sample, and the efficacy of removal of said mycotoxin expressed as a percent reduction in the level of said mycotoxin in said experimental extract as compared to the level of said mycotoxin in said control sample. In the instant invention, said mycotoxin is preferably moniliformin. This methodology allows for the degradation of moniliformin on or within said plants or harvested grain, thus providing improved food grain quality and feed safety.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE I. ISOLATION OF BACTERIA THAT DEGRADE MONILIFORMIN

Various sources of plant material that were likely to naturally contain moniliformin were collected as source material for screening. *Fusarium graminearum*-infested maize kernels (92 independent samples) were obtained from a Pioneer Hi-Bred *Gibberella zeae* (*Fusarium graminearum*) disease nursery.

The metabolism of moniliformin was measured using thin layer chromatography. Microbes were washed from the source material by placing a small amount in a seven milliliter Falcon tube and adding one to two milliliters sterile distilled water (producing "wash fluid"). Maize kernels were split with a razor blade and one to two kernels were used. Tubes were capped and shaken for one to three hours at room temperature. Moniliformin (Sigma Cat No. M5269) was prepared as a solution in mineral salts medium, and was utilized as the only added carbon source. The moniliformin concentration utilized includes but is not limited to 0.75–1.0 milligrams/milliliter in mineral salts medium. The mineral salts medium was prepared by combination of reagents including but not limited to 1.0 g/L ammonium sulfate, 1.0 g/L sodium chloride, 1.0 g/L potassium phosphate, dibasic, 0.2 g/L magnesium sulfate. Sterilization of the solution was accomplished by filtration through a 0.2 micron filter, although various methods for sterilization are available to those skilled in the art. 100 microliters of moniliformin/mineral salts suspension medium was added to each well of a microtiter plate (96 well plate). One microliter of fresh wash fluid was added to each well. Control wells received one microliter of water. After two weeks, one microliter from each well was transferred to a new microtiter plate containing 100 microliters of moniliformin/mineral salts medium. Degradation of moniliformin was assayed by thin layer chromatography (TLC). Silica gel plates containing fluorescent indicator (Whatman 4410 222) were spotted with typically one microgram moniliformin (typically one microliter from assay plates or one microliter of a one miligram/milliliter standard solution). Plates were run using a solvent system of chloroform-ethyl alcohol 3:2. Moniliformin could be seen as a bright blue spot under short-wave UV. Microbial metabolism of moniliformin caused a gradual disappearance of the spot; spots with altered mobility in the TLC system were not detected using this method.

A pure culture of the microorganism responsible for moniliformin degradation was isolated. One microliter was taken from positive wells and added to one milliliter of sterile water. Several ten-fold dilutions were made in sterile water, and 100 microliters from each dilution were plated and spread on YDP agar plates. YDP agar plates were prepared by combination of 10 grams yeast extract (Difco), 20 g/L Bacto peptone, 0.5 g/L dextrose, 15 g/L Bacto agar in water followed by sterilization by autoclaving. From these mixture culture spread plates, individual colonies were streaked for isolation on new YDP plates. An effort was made to choose at least one of every type of bacteria represented on the spread plates. Each bacterium was used to make a dilute suspension in sterile water, and one microliter of this suspension was used to inoculate microtiter wells containing moniliformin in mineral salts as described above.

Initial characterization of bacteria was performed by Gram staining samples. More definitive identification was performed using a combination of techniques. Streak plates of individual bacterial colonies were sent to Microbe Inotech Laboratories, Inc. (St. Louis, Mo.) for tentative identification. The analysis included comparison of bacterial fatty acid methyl esters with Aerobe and Clinical Aerobe databases, and Biolog™ substrate utilization comparison with a Gram negative database. Results of such tests indicate that the bacterial isolate is the Gram negative *Ochrobactrum anthropi* and are demonstrated in Table I. These cultures have been deposited with the American Type Culture Collection (ATCC; 12301 Parklawn Drive, Rockville, Md. 20852 U.S.A.) on Oct. 15, 1996 in accordance with the Budapest Treaty on the International Recognition of the Deposit of Microorganisms for the Purposes of Patent Procedure.

TABLE 1

Microbial isolates having the ability to degrade moniliformin

| ATCC Number | Name | Tentative Identification | Source |
| --- | --- | --- | --- |
| 55846 | MON2906.G1 | *Orchrobactrum anthropi* (Chromobacter) | Moldy corn, from Michigan |
| 55854 | MON2906.B2 | Ochrobactrum anthropi (Chromobacter) | Moldy corn from Michigan |

EXAMPLE II. TREATMENT OF MONILIFORMIN-CONTAMINATED CORN

A. Treatment of contaminated corn in the field

To test the ability of the bacteria isolated by the above-described methodology to degrade or detoxify moniliformin or its derivatives or analogs on maize, mature plants are inoculated with a moniliformin-producing Fusarium sp. and then treated with an appropriate amount of bacteria having the ability to degrade or detoxify moniliformin or its derivatives or analogs. The treatment consists of topically applying a composition comprising an efficacious amount of bacteria onto the tissues of the maize plant such that moniliformin, including any derivatives or analogs of moniliformin, is partially or completely degraded or detoxified.

B. Treatment of contaminated corn after harvest.

A one to ten gram sample of cracked corn is combined or "spiked" with a known amount of moniliformin in ethanol at a concentration of one gram moniliformin per ml of ethanol, followed by mixing to distribute the moniliformin throughout the mixture. A control sample or samples are mixed with solvent alone. The samples are then air-dried to remove excess solvent. The samples are then inoculated with $10^6$ cfu/g of log-phase cells of a microorganism having the ability to degrade moniliformin, designated MON2906.G1 (deposited with the ATCC under accession number ATCC 55846) at a rate of one ml cells per gram, and mixed well to distribute said cells within said sample. Controls are mixed with either cells of said microorganism [designated MON2906.G1, deposited with the ATCC under ATCC accession number 55846] that have been heated to 80° C., such that said cells are non-viable or with cells of a microorganism that does not have the ability to degrade moniliformin. Said mixture is placed in a container, which is then closed and incubated for two weeks at room temperature. At the end of the incubation period, the containers are opened, and the entire contents extracted in a suitable organic solvent to recover the moniliformin. The extract is concentrated and subjected to qualitative and quantitative analysis for detection of moniliformin. The amount of moniliformin is determined and compared to controls. The efficacy of removal of moniliformin is determined by comparison of the percent reduction of the amount of moniliformin in the sample comprising the micoorganism having the ability to degrade moniliformin to the reduction of the amount of moniliformin present in said control sample. The microorganism designated MON2906.B2 (ATCC accession number 55854) is also able to degrade moniliformin, and may be utilized for the above-described purpose.

EXAMPLE III: COMPARISON OF DIFFERENT OCHROBACTRUM ISOLATES

The below listed isolates were streaked out on LB+agar plates and grown at room temperature in ambient light for 5 days. Two media treatments were selected for testing the 12 isolates and a positive and negative control, Medium A: moniliformin, 0.75 ug/ul (Sigma M5269)+mineral salts, or Medium B: moniliformin, 0.75 ug/ul (Sigma M5269)+ mineral salts+Yeast Potato Dextrose (YPD). The mineral salts (per liter) were 1.0 g ammonium sulfate, 1.0 g sodium chloride, 1.0 g potassium, phosphate, dibasic, and 0.2 g magnesium sulfate. The mineral salts were filter sterilized through a 0.2 um filter. The YPD (per liter) was 10 g yeast extract (Difco), 20 g Bacto peptone (Difco), 0.5 g dextrose, and autoclaved or filter sterilized through a 0.2 um filter.

Isolates from the LB agar plates were diluted as follows. A 1 μl loop was touched to a single colony and dispensed into a 2 ml volume of sterile water, vortexed and 20 μl of the first dilution dispensed into another 2 ml volume of sterile water (dilution 2). For the positive control (sample number 8 on Table 2), a plate of mixed culture, 5 different colony types were picked, combined and diluted as above except diluting 20 μl one more time into a 2 ml volume of sterile water (dilution 3). The experiment was performed as follows:

1. 100 μl moniliformin+mineral salts was added to each sample well in a 96-well plate.
2. 5 μl YPD was added to moniliformin+mineral salts+YPD treatment wells.
3. 5 μl of isolate dilution 2 was added to the designated wells except the control wells. Five microliters of dilution 3 to the desired wells for the positive control treatment. Then 5 μl of sterile water was added to the negative control wells.
4. 200 μl water and food coloring was pipetted into the empty wells.
5. The plate was wrapped in parafilm, and stored at room temperature, with ambient light in a clear box.
6. The wells were assayed at day 4 and day 7 by TLC.
7. TLC Assay for moniliformin was done as follows: Slica gel plates containing fluorescent indicator (Whatman 4410 222) were spotted with 0.5 μl (~0.375 ug) from each well of the 96-well assay plate. Plates were run with the solvent system of chloroform:ethanol (3:2). Moniliformin could be seen as a bright blue spot under short-wave UV. Microbial metabolism of moniliformin caused a gradual disappearance of the spot

TABLE 2

Summary of Isolates tested and TLC results

| Sample # | Isolate Description | Source | Comments | Moniliformin degradation by TLC | Result |
|---|---|---|---|---|---|
| 1 (negative control) | none | | water | negative both media treatments | – |
| 2 | MON2906.G1 | moldy corn | ATCC 55846 | positive w/YPD | + |
| 3 | MON2906.E7 | moldy corn | ATCC 55855 | negative both media treatments | – |
| 4 | MON2906.B2 | moldy corn | ATCC 55854 | positive w/YPD | + |
| 5 | ATCC 49237 | soil | ATCC, *Ochrobactrum anthropi* | negative both media treatments | – |
| 6 | ATCC 49187 | exudate | ATCC, *Ochrobactrum anthropi* | negative both media treatments | – |
| 7 | ATCC 49188 | Unknown | ATCC, *Ochrobactrum anthropi* | negative both media treatments | – |
| 8 (positive control) | mixed-moniliformin degraders | moldy corn; seed washate | 5 colonies from plate combined | positive w/moniliformin + mineral salts; not w/YPD | + |
| 9 | ATCC 49687 | Unknown | ATCC, *Ochrobactrum anthropi* | negative both media treatments | – |
| 10 | ATCC 19286 | soil | ATCC, *Ochrobactrum anthropi* | negative both media treatments | – |
| 11 | ATCC 21909 | oil contaminated beach | ATCC, *Ochrobactrum anthropi* | negative both media treatments | – |

Of the 13 isolates (or mixed-culture sample) tested, only strains found on moldy corn degraded moniliformin. One isolate (ATCC 55855) from moldy corn did not degrade moniliformin. Six ATCC isolates of *Ochrobactrum anthropi* tested negative in this assay. Of all of the moniliformin degraders tested and identified, with the exception of the mixed-culture, addition of a small amount of YPD (5ul/100 μl moniliformin+min salts) is necessary to promote growth and moniliformin degradation. When the microorganism is washed from the moldy corn a small amount of a non-moniliformin carbon source is probably also washed onto the plate. Clearly the present invention is able to identify moniliformin degrading enzymes even when a small amount of non-moniliformin carbon source is added to the media Only moniliformin degrading strains were able to grow with moniliformin as the major carbon source.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated bacterium having the ability to degrade moniliformin wherein said bacterium is *Ochrobactrum anthropi* and deposited under ATCC accession number 55846.

2. An isolated bacterium having the ability to degrade moniliformin wherein said bacterium is *Ochrobactrum anthropi* and deposited under ATCC accession number 55854.

* * * * *